United States Patent [19]

Bull

[11] Patent Number: 5,275,953
[45] Date of Patent: Jan. 4, 1994

[54] APPARATUS AND METHOD FOR IN VITRO MANIPULATION OF BLOOD

[76] Inventor: Brian S. Bull, 24489 Barton Rd., Loma Linda, Calif. 92354

[21] Appl. No.: 688,892

[22] Filed: Apr. 22, 1991

[51] Int. Cl.$^5$ .......................... C12Q 1/56; G01N 33/48
[52] U.S. Cl. ........................................ 436/69; 128/763; 128/770; 422/73; 422/100; 422/101; 424/4; 436/70
[58] Field of Search ................. 436/69, 70; 422/73, 422/100, 101; 128/763, 770, 653.4, 655; 424/4; 435/13

[56] References Cited

U.S. PATENT DOCUMENTS

| | | | |
|---|---|---|---|
| 3,631,847 | 1/1972 | Hobbs, II | 128/655 |
| 3,660,037 | 5/1972 | Sokol | 436/70 X |
| 3,854,324 | 12/1974 | Altshuler et al. | 436/69 X |
| 3,888,239 | 6/1975 | Rubinstein | 128/655 |
| 4,579,828 | 4/1986 | Ali | 436/69 X |
| 4,765,179 | 8/1988 | Fuller et al. | |

Primary Examiner—Jill A. Johnston
Attorney, Agent, or Firm—Flehr, Hohbach, Test, Albritton & Herbert

[57] ABSTRACT

A blood extracting and receiving container assembly (10) having a coating agent (22) disposed on an interior surface of a blood receiving chamber (12) and an extracting apparatus (14) to effectively isolate a blood specimen from contacting surfaces which would initiate clotting. The coating agent contains molecules which inhibit the activation of blood elements responsible for initiating blood clotting processes. A method for manipulating a blood specimen in vitro in association with the subject blood extracting and receiving assembly (10) includes the steps of coating an interior surface of the extracting and receiving container assembly (10) with nonthrombogenic coating agent (22), and, while coating agent (22) adheres to the interior surface of assembly (10), withdrawing a blood specimen (24) into the assembly. Additionally, the method includes the steps of exposing the specimen to an activating surface in a controlled manner to initiate blood clotting processes, preferably while a portion of the specimen is admixed with the nonthrombogenic agent. A clotting parameter, such as weight or clotting rate, may be correlated with a disease condition.

21 Claims, 3 Drawing Sheets

APPARATUS AND METHOD FOR IN VITRO MANIPULATION OF BLOOD

TECHNICAL FIELD

This invention relates to a novel apparatus and method for manipulating blood in vitro to perform diagnostic testing, and, more specifically, this invention relates to an apparatus and method for manipulating blood in vitro to measure the thrombotic potential of the blood.

BACKGROUND ART

In the medical field, it is often desirable to measure the thrombotic potential of blood, the tendency of blood to form a clot, and cardiologists have been using such measurements to predict the progression of diseases such as atherosclerosis and heart disease. In recent years, cardiologists have collected data indicating that blood elements play a significant role in heart disease and have concluded that blood clots are the primary cause of the majority of heart attacks.

The accumulating evidence has led to a scientific explanation of the correlation between heart disease and blood clotting processes. More specifically, areas of blood vessels that are covered with fatty plaques become brittle, causing the vessels to crack and fissure as the vessel is stretched. Tiny rifts in the vessel wall expose collagen which attracts formed elements in the blood known as platelets. The platelets aggregate near the rift and adhere to the collagen to restrict blood flow and initiate clotting processes. Cardiologists propose that heart attacks occur when a clot intended to repair a rift in a vessel wall grows too aggressively, blocking the entire passage and obstructing blood flow to the heart.

A significant medical advantage may be gained by using measurements of the clotting process in vitro to predict the likelihood of similar blood clotting processes occurring in vivo. Such measurements can be used to identify patients at greatest risk of heart attacks or strokes by reproducing in vitro the circumstances that lead to these maladies. Early detection of a highly reactive clotting response in a patient's blood permits a physician to treat the patient for excessive blood clotting activity to reduce the patient's susceptibility to heart attack or stroke.

In the past, apparatuses have been devised for evaluating the blood clotting process and associated platelet response of a blood specimen. However, problems with these apparatuses have arisen. Transfer of blood from a patient's circulatory system to the diagnostic apparatus significantly alters the blood elements responsible for clotting, specifically, the blood platelets and plasma protein-clotting factors. When a blood specimen is exposed to a surface other than healthy endothelial tissue, such as glass or other artificial surfaces, blood platelets in the specimen contact the foreign surface and become activated. Blood platelets immediately identify any synthetic blood container as foreign. Likewise, plasma protein-clotting factors, primarily factors VII and XII, become activated upon contact with damaged tissue or a foreign surface to initiate blood coagulation.

These changes significantly affect the transferability of observations on blood in vitro to conclusions about in vivo behavior. Moreover, analysis of the blood specimen using these prior art apparatuses typically requires centrifugation to remove the cellular components of the blood sample, resulting in further alteration of the blood from its state in the bloodstream.

Present procedures for evaluating blood clotting processes attempt to delay the above-described changes by adding anticoagulants, such as sodium citrate, to the blood specimen. Prior to evaluating the clotting potential of the specimen, the effect of the anticoagulant is reversed. However, since the blood was previously exposed to the abnormal surfaces of the blood evaluation device, some clotting factors are partially, or completely, activated, and many of the platelets also have become activated, including undergoing a shape change known as the disk/sphere transformation. Thus, in many respects, the blood specimen has begun the clotting process before diagnostic testing begins, and it becomes difficult to determine the blood specimen's original thrombotic tendency.

As an alternative to treating the blood specimen with anticoagulants, a class of blood evaluation devices has been devised to compensate for any minor activation of blood elements by massively activating the blood specimen immediately upon withdrawal from the bloodstream. These devices, generally referred to as whole blood coagulation analyzers, intermix a thrombogenic material, such as ground glass or diatomaceous earth, with the blood specimen to rapidly induce complete activation. Tests using this method of rapid activation, however, produce inconclusive results because clotting occurs too rapidly to distinguish excessively active clotting processes from healthy clotting processes.

Additionally, if blood can be withdrawn and studied in vitro without clotting and without the necessity to mix an anticoagulant with it, it is believed that characteristics other than clotting can be much more accurately observed.

The difficulties suggested in the preceding are not intended to be exhaustive but rather are among many which tend to reduce the accuracy, effectiveness, and physician satisfaction with prior apparatuses and associated methods for testing blood clotting processes. Other noteworthy problems may also exist; however, those presented above should be sufficient to demonstrate that such methods and apparatuses appearing in the past will admit to worthwhile improvement.

Accordingly, it is therefore a general object of the invention to provide an apparatus and method for manipulating blood in vitro which will obviate or minimize difficulties of the type previously described.

It is a specific object of the invention to provide a blood extracting and receiving assembly which permits recovery of a blood specimen from a patient for determining the thrombotic tendency of the patient's blood.

It is another object of the invention to provide a blood extracting and receiving assembly which may be used to identify individuals at high risk of maladies resulting from excessive blood clotting activity and to monitor high risk individuals during specific therapy to decrease the clotting activity.

It is still another object of the invention to provide a blood extracting and receiving assembly which maintains a blood specimen in vitro in essentially the same state as found in vivo.

It is a further object of the invention to provide a blood extracting and receiving assembly which alleviates the necessity of adding anticoagulants to the blood specimen and then reversing their effects prior to performing diagnostic testing.

It is yet a further object of the invention to provide a blood extracting and receiving assembly which is self contained, disposable, and economical to manufacture.

It is still a further object of the invention to provide a method for inhibiting activation of blood elements, specifically platelets, and those blood clotting factors which become activated upon exposure to an unnatural surface.

It is yet another object of the invention to provide a method for determining the thrombotic tendency of a blood specimen under sufficiently controlled conditions to permit discrimination between clotting rates which are dangerously high and those that are within an acceptable range.

DISCLOSURE OF THE INVENTION

A preferred embodiment of the invention which is intended to accomplish at least some of the foregoing objects includes a coating agent disposed on an interior surface of a blood extracting and receiving assembly. The extracting and receiving assembly includes a blood receiving chamber and a blood extracting member, such as a needle, which communicates with the blood receiving chamber to permit the passage of the coating agent and a blood specimen into the chamber. The coating agent contains molecules which inhibit the activation of blood elements responsible for initiating blood clotting processes, and the agent effectively isolates the blood specimen from contacting the interior wall of the blood receiving chamber until controlled clotting is initiated.

A method for manipulating a blood specimen in vitro, in association with the blood extracting and receiving assembly of the present invention, includes the steps of coating an interior surface of an extracting and receiving assembly with a viscous, nonthrombogenic coating agent, and, while the coating agent adheres to the interior surface of the assembly, withdrawing a blood specimen into the assembly. The coating agent serves to prevent the blood specimen from contacting the interior surface of the blood extracting and receiving assembly.

In another aspect of the invention, a method for determining the thrombotic tendency of a blood specimen, in accordance with a preferred embodiment of the subject invention, includes the additional step of exposing the specimen to an activating surface in a controlled manner to simulate the in vivo situation whereby native blood not admixed with an anticoagulant is exposed to the surface of an atheromatous plaque and thus to activate blood platelets and blood proteins susceptible to contact activation to initiate blood clotting processes.

BRIEF DESCRIPTION OF THE DRAWINGS

Other objects and advantages of the present invention will become apparent from the following detailed description of a preferred embodiment thereof taken in conjunction with the accompanying drawings, wherein.

BEST MODE OF CARRYING OUT THE INVENTION

Figure 1:
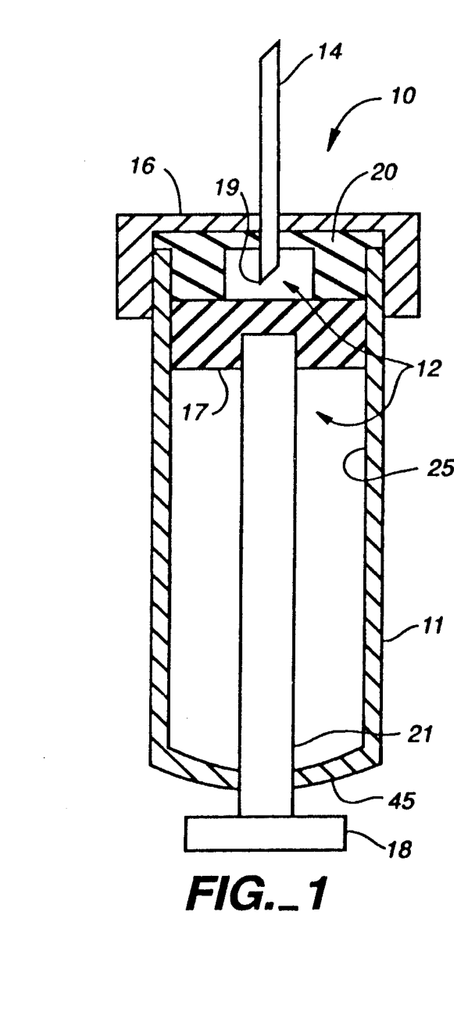
FIG. 1 is a side elevation view, in cross section, of a schematic representation of a blood extracting and receiving assembly in accordance with a preferred embodiment of the invention.

Referring now to the drawings, wherein like numerals indicate like parts, and initially to FIG. 1, there will be seen a blood extracting and receiving assembly, generally designated 10, which advantageously can take the form of a hypodermic syringe and needle. The syringe portion includes walls 11 defining a sealed blood receiving chamber 12 in which a plunger assembly, generally designated 15, is movably mounted. Plunger 15 has an inner end 17 which is in sliding and sealed engagement with the interior surface of walls 11, and plunger 15 also has an outer manually engageable end 18. A hollow tubular needle 14 is mounted to a cap member 16 for extracting a blood specimen from a patient. Affixed to an open end of the blood receiving chamber 12 is an elastomeric diaphragm 20, which permits the passage of sharp inner end 19 of a piercing needle 14 therethrough and into blood receiving chamber 12.

Using conventional techniques, when a blood specimen is exposed to the interior glass or plastic surface of the chamber, blood clotting processes are induced at the blood-surface interface. The present invention, however, prevents the initiation of blood clotting and enables controlled in vitro manipulation and testing of blood specimens under what amounts to in vivo conditions.

Figure 2:
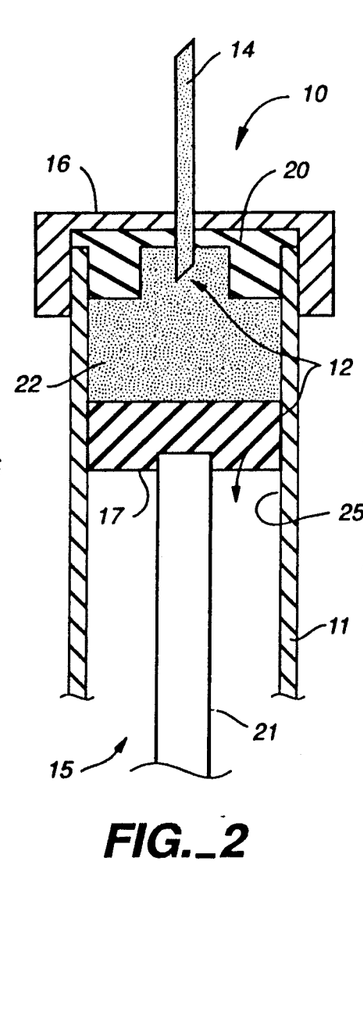
FIG. 2 is a side elevation view, in cross section, of the subject blood extracting and receiving assembly having a coating agent disposed therein.

A present method for manipulating blood in vitro, while maintaining the blood in essentially the same state as occurs in vivo, will now be described in association with FIGS. 2 and 3. Prior to withdrawal of a blood specimen from a patient, a coating agent 22 must be positioned in the blood extracting and receiving assembly, for example, by drawing a liquid coating agent through needle 14 into blood receiving chamber 12, as shown in FIG. 2 (by moving plunger 15 in a downward direction). Coating agent 22 must be a nonthrombogenic material which either forms a wall 11 or is deposited as a coating on wall 11. As used herein the expression "nonthrombogenic" materials shall include liquid or solid materials which do not activate platelets or blood clotting intermediaries and materials which may activate platelets but simultaneously destroy or inhibit the effectiveness to prevent further extension of platelet clotting function or further continuation of other blood clotting processes. The most suitable nonthrombogenic materials presently known are ionic radiographic contrast agents. Such ionic contrast agents are fluids capable of being drawn into a specimen container such as a hypodermic syringe; they are viscous and will therefore adhere to the interior surfaces of the needle and syringe; and they have a significantly different density than native blood to make rapid gravity separation possible. In addition, such agents in their usual formulation contain molecules that prevent stimulation of the clotting pathways through activation of clotting intermediates and through activation of platelets.

When a fluid radiographic contrast agent 22 is employed, it is drawn into sealed chamber 12 by plunger 15, and any air or gas in the chamber exhausted or expelled by elevating the needle. As shown in FIG. 2, chamber 12, between the plunger and needle, and needle 14 is filled with the nonthrombogenic coating agent and, therefore, is sealed against the entry of air or other materials which might cause blood clotting. To the extent that the sliding seal between inner plunger end 17 and wall 11 is not an air-tight seal, viscous coating agent 22 ensures such a seal.

It has been observed in the past in connection with radiographic studies that a bolus, or blood clot, will not form in the presence of ionic radiographic contrast agents in vitro. In the present invention, therefore, such agents are preferably used as coating agents to prevent clotting. Ionic radiographic contrast agents generally consist of fully substituted benzene rings having three molecules of iodine, and an attached group, typically a meglumine sodium group. Incidental to their main purpose of providing radiopacity, such agents inhibit activation of both platelets and blood clotting factors and, thus, prevent initiation of blood clotting processes.

There are two types of ionic contrast agents currently in use. Both are hyperosmolar, that is, have an osmolarity in excess of the osmolarity of blood plasma. Ionic contrast agents formed from single benzene rings have an osmolarity of about 1500 millimoles per liter (five times blood plasma), while new contrast agents formed from dimerized benzene rings have an osmolarity as low as 600 millimoles per liter. The dimerized ionic contrast agents have two benzene rings with six iodine molecules and a cationic and anionic group on each benzene ring.

There are radiographic contrast agents formed from benzene rings which do not have the anionic and cationic groups. These contrast agents are not "ionic" and are not suitable for use with the present invention since they will not inhibit blood clotting, even though they are quite suitable for use in radiographic applications. The property of opacity to gamma rays is not being employed in the present invention.

Instead, the coating agent of the present invention must have ionic groups which inhibit activation of the clotting factors and the platelets; it must be sufficiently viscous to adhere to the container or specimen receiving chamber walls long enough to enable withdrawal of the blood specimen and setting the blood specimen chamber up for controlled clotting; and it preferably has a density which differs from native blood (most preferably greater than native blood). It is hypothesized it is the meglumine sodium group which is most useful to the method of the present invention. It will be understood, however, that other nonthrombogenic coating agents may be found to exhibit the properties required for use with the blood specimen chamber which will substantially inhibit platelet activation and prevent initiation of the blood clotting processes.

Figure 3:
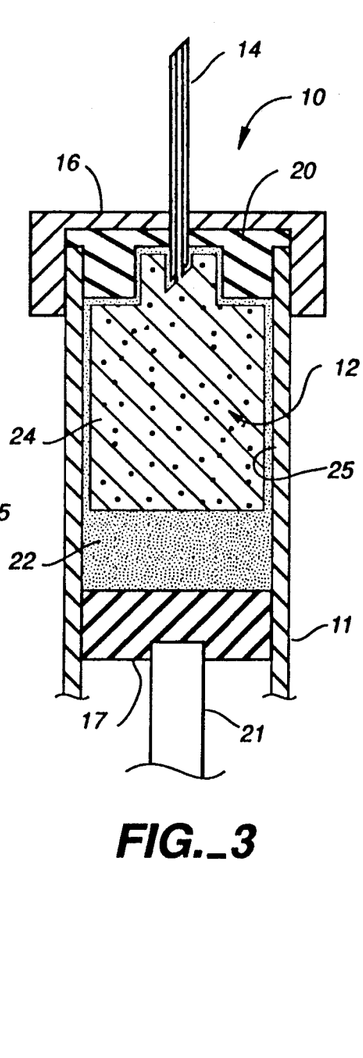
FIG. 3 is a side elevation view, in cross section, of the subject blood extracting and receiving assembly following withdrawal of a blood specimen from a patient.

Turning to FIG. 3, blood extracting and receiving assembly 10 is shown after withdrawal of a blood specimen 24 from a patient. Coating agent 22, which has a high viscosity, adheres to an interior surface 25 of the blood receiving chamber and needle as the syringe plunger is moved away from needle 14 to extract native blood directly from the patient and to pull a blood specimen 24 into chamber 12. The coating or layer of agent 22 along the interior surface 25 of the syringe, and the interior of needle 14, effectively isolates blood specimen 24 from the interior surface of the blood receiving chamber and needle. Ionic contrast agents are highly viscous and mix relatively slowly with blood due to their viscosity and differences in density between the contrast agents and blood. The contrast agents are very dense because of the iodine atoms, and they settle in the bottom of the blood receiving chamber, while the blood "floats" near the top of the chamber. This separation facilitates withdrawal of the specimen into the upper portion of the blood receiving chamber and maintains the unclotted integrity of the blood specimen. As will be understood, agents which have a viscosity higher than blood and a density which is lower would also be suitable, although the coating agent would then float on the blood specimen.

Figures 5, 6A, 6B, 6C, 8:
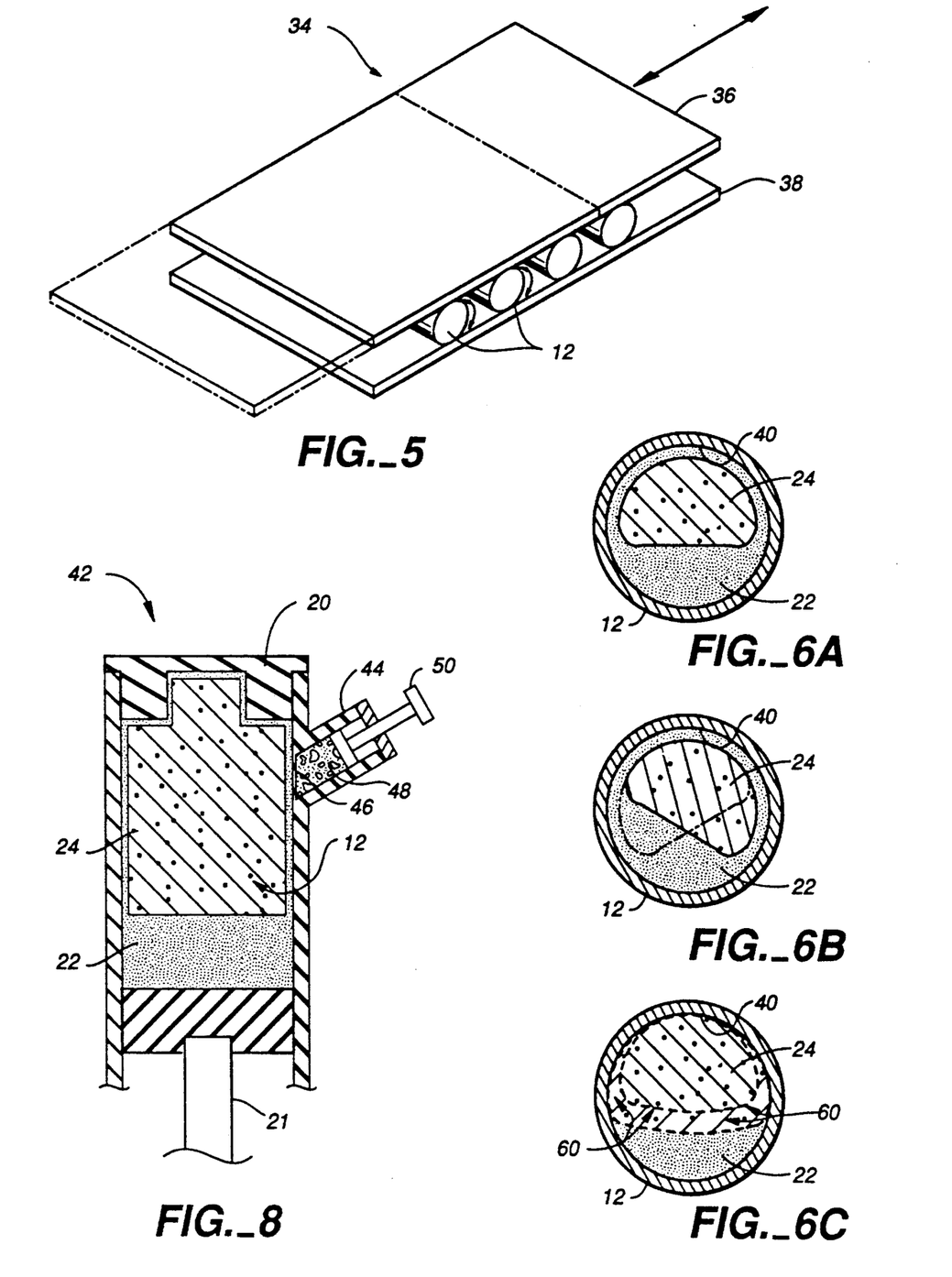
FIG. 5 is a top perspective view of a schematic representation of an oscillatory device for exposing a blood specimen in the blood extracting and receiving assembly to an activating surface to initiate clotting processes.
FIGS. 6a-6c are enlarged end views, in cross section, of the subject blood extracting and receiving assembly depicting exposure of a blood specimen to an activating surface utilizing the oscillatory device of FIG. 5.
FIG. 8 is a side elevation view, in cross section, of a schematic representation of an alternative embodiment of the subject blood extracting and receiving assembly.

Turning now to FIG. 5, there will be seen an oscillatory device 34 for exposing a blood specimen to the interior surf ace of blood receiving chamber 12 under controlled conditions. Oscillatory device 34 initiates clotting processes by gently oscillating the blood receiving chamber, causing the blood specimen to wash against the viscous coating agent and gradually remove the coating agent from a portion of the interior surface of the chamber and become admixed with a portion of the coating agent. The gentle oscillation resembles blood flow conditions occurring in the bloodstream, and so exposure to the activating surfaces of the blood receiving chamber mimics exposure to a foreign surface in vivo. Once an area of chamber wall is exposed, f or example surface 40 in FIG. 6C, the blood platelets and blood clotting elements will react to the glass or plastic surface as foreign and begin the clotting process.

Figure 4:
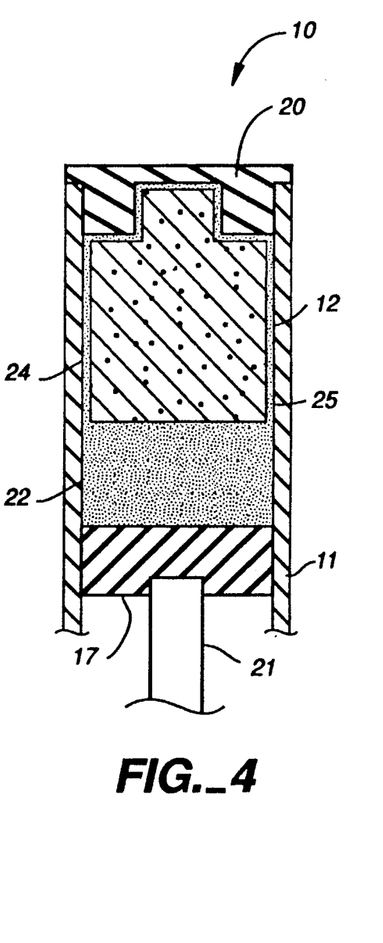
FIG. 4 is a side elevation view, in cross section, of the subject blood extracting and receiving assembly after removal of the blood extracting needle assembly.

In order to prepare blood receiving chamber 12 for oscillation, needle 14 and needle stabilizing end cap 16 preferably are removed from the blood receiving chamber (FIG. 4), and the chamber is placed horizontally in an oscillatory device 34 (FIG. 5). In the embodiment of FIG. 5, a plurality of blood receiving chambers are disposed between a pair of horizontal plates 36 and 38 and rotated by being rolled from side-to-side about their longitudinal axes by approximately 45°. Each roll cycle has a period approximately equal to 25 seconds.

FIGS. 6A-6C depict the effect of rolling blood receiving chamber 12 in oscillatory device 34. Initially, the blood "floats" above the ionic contrast agent near the upper interior surface 40 of blood receiving chamber 12, as shown in FIG. 6A. As chamber 12 is rotated from side-to-side, the blood gently washes the ionic contrast agent away from interior surface 40 and begins to mix with the nonthrombogenic agent, as seen in FIG. 6B. FIG. 6C shows the blood specimen touching interior surface 40 following sufficient oscillatory rotation to expose interior surface 25 of the specimen receiving chamber. Additionally, a region or portion 60 between native blood 24 and nonthrombogenic agent 22 is comprised of a mixture of blood and the nonthrombogenic agent.

Blood clotting is a process which will continue to completion, that is, until all the available clottable constituents of the blood have clotted. Thus, given enough time and the absence of inhibitors, a specimen of blood which has a relatively low or safe clotting rate will produce clotted blood in an amount which is not distinguishable from a similar specimen having a dangerously high clotting rate. Accordingly, merely causing the clotting of two specimens and then weighing the resulting clot will not produce data which will be capable of accurate correlation to thrombosis rates which are dangerous.

Ideally, a non-invasive blood clotting rate measurement would be highly desirable for use with the non-thrombogenic blood specimen extraction process of the present invention. It is believed that such measurements and a time profile may be achievable using a time domain spectroscopy technique, such as is set forth in U.S. Pat. No. 4,765,179 to Fuller et al. if measurement of the clotting can take place during the oscillating process without influencing the process, the possibility for statistical correlation of the blood clotting rate with disease conditions and thrombosis potential should be possible.

An important feature of the method of the present invention, however, is that the use of a liquid nonthrombogenic agent in the blood containing chamber also allows data to be obtained as to clotting rates. As may be seen in FIG. 6C, oscillation of the blood specimen container not only washes agent 22 from the top interior surface 40 of container 12, it also produces a region 60 in which a portion of the blood specimen is admixed with nonthrombogenic material 22. Such mixing of blood with the nonthrombogenic agent has the effect of preventing clotting of a portion of specimen 24, but such mixing occurs slowly as a result of the viscous and dense nature of the preferred nonthrombogenic material, namely, an ionic radiographic contrast agent.

For blood specimens having a high rate of clotting, the clotting process will be initiated upon contact with surface 40 and will proceed relatively rapidly to completion before inhibited region 60 grows significantly in volume. Slower clotting specimens will admix with agent 22 to a substantial degree before they clot. Using a viscous, dense, liquid nonthrombogenic agent in specimen extraction and containment assembly 12, therefore, enables the quantity of the clotting produced to be correlated to the rate of clotting.

In the method of the present invention, therefore, containers 12 can be oscillated for a time period sufficient to ensure clotting of all available uninhibited clotting constituents, for example, 25 to 30 minutes. The containers then can be opened, or even broken, and the liquid, non-clotted materials drained from the clotted constituents, for example, by a sieve. The clotted constituents can then be weighed. In rapidly clotting blood the clot weight will be significantly greater than the clot rate for a more normal slowly clotting specimen, even though both specimens were the same size and oscillated for the same length of time. The admixing of nonthrombogenic material with the slower clotting blood will prevent a larger portion of the blood specimen from clotting.

Figure 7:
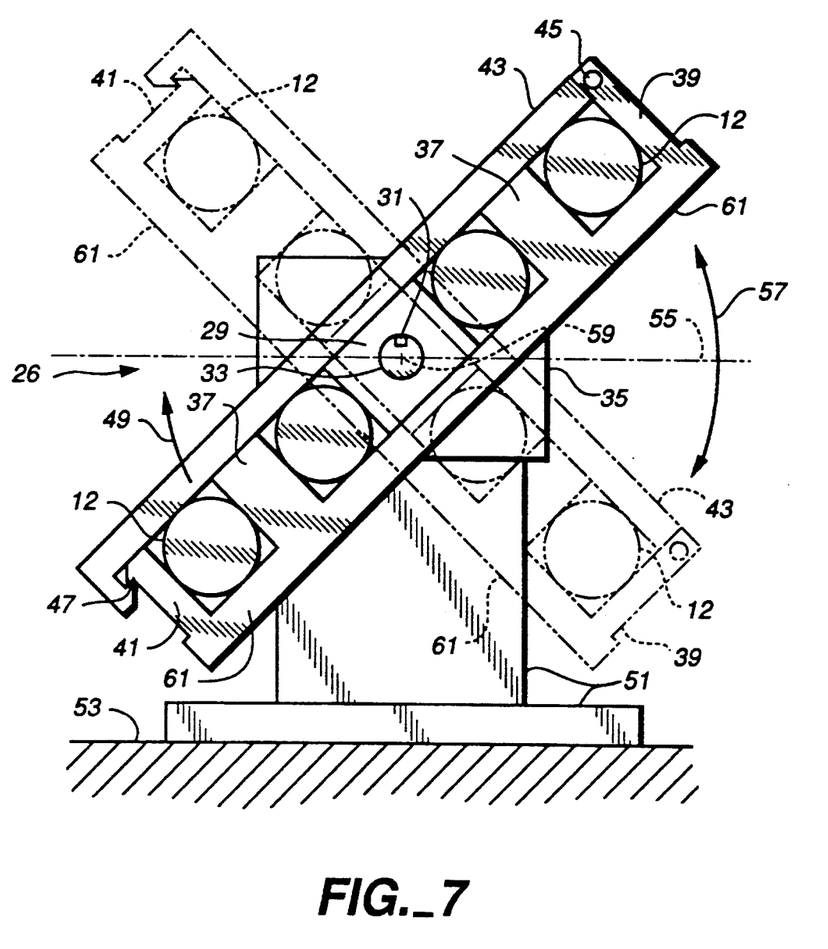
FIG. 7 is an end elevation view of a schematic representation of an alternative embodiment of an oscillatory device for exposing a blood specimen in the blood extracting and receiving assembly to an activating surface to initiate clotting processes.

An alternative embodiment of an assembly suitable for oscillating or agitating unclotted blood specimens in containers 12 is shown in FIG. 7. Oscillatory device 26 is provided by a rack which receives tubes 12 and holds the same with the longitudinal axes of the tubes generally horizontally oriented. In the preferred form the rack assembly includes a central body portion 29 keyed at 31 for rotation with shaft 33 of motor 35. Extending laterally, preferably from both sides of central body position 29, are arm portions 61. Tube receiving spaces or pockets on arm portions 61 are defined by partitions 37 and end walls 39 and 41. In order to facilitate mounting and securement of the tubes in tilting rack assembly 26, a rack closure member 43 is pivoted to end wall 39 at 45 and latched to end wall 41 at latch 47.

In use, closure 43 is unlatched and pivoted in the direction of arrow 49 to an open position to permit mounting of elongated tubes 12 in the rack. The closure is then latched closed to secure the tubes in the tiltable rack. Motor 35, which is mounted by stand 51 to elevate the assembly above support surface 53 by a sufficient distance to enable oscillation, is then turned on and arm portions 61, and thus tubes 12, are oscillated about horizontal plane 55, preferably by about 45 degrees above and below plane 55, as indicated by arrow 57 and the phantom lines in FIG. 7 Tubes 12 are thereby rotated by tilting about a tilt axis 59 which is substantially parallel to the longitudinal axis of each tube. This tilting preferably is accomplished by a slow oscillation having a complete cycle of about 25 seconds, and it has the effect of gradually washing the coating agent from the interior surfaces of the blood containing chamber.

While both illustrated embodiments show tubes 12 with their longitudinal axes in a horizontal orientation, it will be understood that the tubes could be positioned with vertically oriented longitudinal axis and tilted about a transverse horizontal axis.

The apparatus and method of the present invention, therefore, permits withdrawal and manipulation of blood in vitro in a manner closely resembling the clotting process in vivo. Moreover, it is hypothesized that since clotting now will take place in unadulterated blood, data as to a clotting parameter, for example clotting rates and/or clotting amounts, will be sufficiently statistically accurate to enable correlation of the same to a disease condition, such as the risk of heart attacks through thrombosis. Thus, the present process further includes the step of correlating a clotting parameter with disease conditions to permit medical intervention.

Limited testing in which containers are opened and the clots weighed has been undertaken, and marked differences in the quantity of clotting have been observed from specimen to specimen. Obviously, lesser oscillation times also can be used before quantifying the amount of clotting which has taken place.

As an alternative to the above-described method of controlled oscillation to induce clotting in blood, a foreign surface having high surface area, such as diatomaceous earth or ground glass, may be introduced, for example by injection through end cap 20, into blood receiving chamber 12 to initiate the clotting process. Another method of inducing blood clotting processes involves injecting a gas into the blood receiving chamber. Air alone will start the process, but it is a relatively slow initiator, and an aerosol with a finely divided particulate, such as silica, is preferred.

In this connection, FIG. 9 shows a blood extracting and receiving assembly 4 2 for introducing a high surf ace area substance into the blood receiving chamber. Blood extracting and receiving assembly 42 includes an auxiliary channel 44 having a frangible diaphragm 46 extending across channel 44. Diatomaceous earth, ground glass or other high surface area materials 48 may be introduced into blood receiving chamber 12 by urging auxiliary plunger 50 toward diaphragm 46 to push clotting substance 48 into chamber 12.

Though blood clotting is the diagnostic parameter primarily discussed in connection with the subject blood extracting and receiving assembly 10, it is to be understood that other diagnostic tests may be performed using the subject invention. For example, assemblies 10 and 42, shown in FIGS. 1-4 and 8, may be used to test the reaction of a blood specimen to various drugs by introducing the drugs into the blood specimen by injection through end diaphragm 20 or insertion through auxiliary channel 44.

After reading and understanding the foregoing inventive apparatus and method of manipulating blood in vitro, in conjunction with the drawings, it will be appreciated that several distinct advantages of the subject invention are obtained.

Maintenance of the blood in vitro in a state similar to that occurring in vivo permits a physician to observe the rapidity and extent of a patient's blood clotting process under controlled conditions. Thus, the subject blood extracting and receiving assembly 10 may be used to identify individuals at high risk to maladies resulting from excessive blood clotting activity.

Moreover, combining a coating agent which hinders the activation of blood clotting processes with a blood receiving chamber results in medical instrument for use in determining the thrombotic tendency of a blood specimen which alleviates the necessity of centrifuging the blood specimen or adding anticoagulants to the blood specimen prior to preforming diagnostic testing.

In addition, the blood receiving chamber of the present invention remains completely sealed during the diagnostic testing process to effectively isolate the blood specimen from airborne contaminants and to protect technicians manipulating the blood specimen from any infective agent present in the specimen.

In describing the invention, reference has been made to a preferred embodiment and illustrative advantages of the invention. Those skilled in the art, however, and familiar with the instant disclosure of the subject invention, will recognize additions, deletions, modifications, substitutions, and other changes which will fall within the purview of the subject invention and claims.

What is claimed is:

1. A method for containing a blood specimen in vitro comprising the steps of:
providing an interior surface of a blood specimen extracting and receiving container assembly with a layer of an ionic radiographic contrast agent; and
while said agent is provided on said interior surface of said specimen extracting and receiving container assembly, withdrawing a blood specimen from a patient and depositing said specimen into said specimen extracting and receiving container assembly.

2. The method as defined in claim 1 wherein:
said providing step is accomplished by coating an interior surface of said blood specimen extracting and receiving container assembly with said agent.

3. The method as defined in claim 2 wherein:
said agent has a greater density and viscosity than blood.

4. The method as defined in claim 3 wherein:
after said withdrawing step, exposing said blood specimen to an activating means to initiate blood clotting, and
during said exposing step, mixing said blood specimen with said coating agent.

5. The method as defined in claim 4 wherein:
after said exposing step and said mixing step, quantitatively measuring clotted blood in said specimen.

6. The method as defined in claim 2, and the additional step of:
after said withdrawing step, exposing the blood specimen to an activating means in a controlled manner to initiate blood clotting.

7. The method as defined in claim 6, and the additional step of:
after said exposing step, correlating a clotting parameter with a disease condition.

8. The method as defined in claim 6 wherein:
said exposing step is accomplished by introducing a blood clot inducing means into said chamber of said blood extracting and receiving assembly.

9. The method as defined in claim 6 wherein:
after said exposing step, measuring the amount of clotting during the clotting process.

10. The method as defined in claim 9 wherein:
said measuring step is accomplished while the clotted blood remains within said chamber.

11. The method as defined in claim 6 wherein:
said exposing step is accomplished by periodically displacing a chamber of said specimen extracting and receiving container assembly until motion of the blood specimen in said chamber removes a portion of said coating agent from said interior surface of said chamber and said blood specimen contacts an uncoated area of said interior surface.

12. The method as defined in claim 11 wherein:
said specimen receiving chamber is an elongated tube; and
said displacing step is accomplished by mounting said elongated tube in a horizontal orientation and rotating said elongated tube about a longitudinal axis of said elongated tube.

13. The method as defined in claim 12 wherein:
said elongated tube is rotated by rolling said elongated tube along a horizontal plane by a distance so that any point on said elongated tube travels through an arc length subtended by an angle up to about 45°.

14. The method as defined in claim 13 wherein:
said elongated tube is rolled in one direction and then rolled in an opposite direction over a roll cycle of approximately 25 seconds.

15. The method as defined in claim 12 wherein:
said elongated tube is rotated by tilting said tube about a tilt axis substantially parallel to said longitudinal axis.

16. The method as defined in claim 15 wherein,
said tilting step is accomplished by oscillatory tube supporting means carrying said tube about mid tilt axis by about 45° above and about 45° below a horizontal plane.

17. An assembly for maintaining blood in vitro in essentially the same rate as occurs in vivo comprising:
a chamber for receiving a blood specimen;
an ionic radiographic contrast agent provided as a coating on an interior surface of said chamber to prevent contact between the blood specimen and thrombotic initiating surface; and
a blood specimen contained in a volume of said chamber interiorly of said coating of said ionic radiographic contrast agent.

18. The assembly as defined in claim 17 wherein:
said agent is a liquid having a density and viscosity greater than blood.

19. The assembly as defined in claim 17 wherein:
said agent is a liquid having a viscosity greater than blood and a density less than blood.

20. The assembly as defined in claim 17, and
extracting means communicating with said chamber for the passage of blood into said chamber, said ionic radiographic contrast agent being provided as a coating on an interior surface of said extracting means.

21. A method for containing a blood specimen in vitro comprising the steps of:
coating an interior surface of at least a portion of a container assembly with an ionic radiographic contrast agent to prevent contact of said interior surface in said portion of said container assembly by said blood specimen; and
while said agent is coated on said interior surface, withdrawing a blood specimen from a patient into said portion of said container assembly.

* * * * *

UNITED STATES PATENT AND TRADEMARK OFFICE
CERTIFICATE OF CORRECTION

PATENT NO. : 5,275,953

DATED : JANUARY 4, 1994

INVENTOR(S) : Brian S. Bull

It is certified that error appears in the above-identified patent and that said Letters Patent is hereby corrected as shown below:

Column 2, line 22, delete "f rom" and insert ---from---.

Column 3, line 35, delete "surf ace" and insert ---surface---.

Column 6, line 26, delete "surf ace" and insert ---surface---.

Column 6, line 37, delete "f or" and insert ---for---.

Column 7, line 16, delete "if" and insert ---If---.

Column 8, line 45, delete "f rom" and insert ---from---.

Column 8, line 60, delete "4 2" and insert ---42---.

Column 10, claim 11, line 27, delete "coating".

Column 10, claim 17, line 57, delete "rate" and insert ---state---.

Signed and Sealed this

Seventeenth Day of May, 1994

*Attest:*

BRUCE LEHMAN

*Attesting Officer*     *Commissioner of Patents and Trademarks*